US008086319B2

(12) United States Patent
van Dijk (10) Patent No.: US 8,086,319 B2
(45) Date of Patent: Dec. 27, 2011

(54) COCHLEAR IMPLANT FITTING (75) Inventor: Bas van Dijk, Mechelen (BE)

(73) Assignee: Cochlear Limited, Macquarie University, NSW (AU)

( * ) Notice: Subject to any disclaimer, the term of this patent is extended or adjusted under 35 U.S.C. 154(b) by 548 days.

(21) Appl. No.: 11/125,334

(22) Filed: May 10, 2005

(65) Prior Publication Data

US 2005/0261748 A1 Nov. 24, 2005

(30) Foreign Application Priority Data

May 10, 2004 (AU) ................................ 2004902462

(51) Int. Cl.
 A61N 1/05 (2006.01)
(52) U.S. Cl. .............. 607/57; 607/55; 607/56; 607/137; 600/559; 600/379
(58) Field of Classification Search .............. 607/55–57, 607/137; 600/559, 379
 See application file for complete search history.

(56) References Cited

U.S. PATENT DOCUMENTS

| 4,261,372 | A |   | 4/1981  | Hansen et al. |        |
|-----------|---|---|---------|---------------|--------|
| 4,487,210 | A |   | 12/1984 | Knudsen et al.|        |
| 4,532,930 | A |   | 8/1985  | Crosby et al. |        |
| 5,143,090 | A |   | 9/1992  | Dutcher et al.|        |
| 5,594,174 | A |   | 1/1997  | Keefe         |        |
| 5,626,629 | A |   | 5/1997  | Faltys et al. |        |
| 5,758,651 | A | * | 6/1998  | Nygard et al. | 600/554|
| 5,776,179 | A | * | 7/1998  | Ren et al.    | 607/137|
| 5,792,072 | A |   | 8/1998  | Keefe         |        |
| 5,922,017 | A |   | 7/1999  | Bredberg et al.|       |
| 5,991,663 | A | * | 11/1999 | Irlicht et al.| 607/57 |
| 6,070,105 | A |   | 5/2000  | Kuzma         |        |
| 6,119,044 | A |   | 9/2000  | Kuzma         |        |
| 6,157,861 | A | * | 12/2000 | Faltys et al. | 607/57 |
| 6,163,729 | A |   | 12/2000 | Kuzma         |        |
| 6,231,604 | B1| * | 5/2001  | von Ilberg    | 623/10 |
| 6,259,951 | B1|   | 7/2001  | Kuzma et al.  |        |
| 6,308,101 | B1|   | 10/2001 | Faltys et al. |        |
| 6,415,185 | B1|   | 7/2002  | Maltan        |        |
| 6,487,453 | B1|   | 11/2002 | Kuzma et al.  |        |

(Continued)

FOREIGN PATENT DOCUMENTS

AU 2005201999 11/2005

(Continued)

OTHER PUBLICATIONS

Gantz et al., "Combining Acoustic and Electrical Hearing," Laryngoscope, 113 (Oct. 2003), pp. 1726-1730.

(Continued)

Primary Examiner — Carl H Layno
Assistant Examiner — Natasha Patel
(74) Attorney, Agent, or Firm — Kilpatrick, Townsend & Stockton, LLP.

(57) ABSTRACT

A method for fitting a cochlear prosthesis to a cochlea having residual acoustic hearing capability, in order to exploit the residual acoustic hearing capability to the extent possible. A portion of the cochlea having residual acoustic hearing capability is determined by measuring the neural response to acoustic and/or electrical stimulations. Electrical stimulations are applied only to the portions of the cochlea lacking acoustic hearing capability, or possessing only partial acoustic hearing capability. Surgical implantation depth may be optimised by the method, and/or a patient map may be suitably defined to implement the method.

36 Claims, 6 Drawing Sheets

U.S. PATENT DOCUMENTS

| | | |
|---|---|---|
| 6,498,954 B1 | 12/2002 | Kuzma et al. |
| 6,556,870 B2 | 4/2003 | Zierhofer |
| 6,628,991 B2 * | 9/2003 | Kuzma et al. .................. 607/137 |
| 6,754,537 B1 | 6/2004 | Harrison |
| 6,889,094 B1 | 5/2005 | Kuzma et al. |
| 6,915,166 B1 * | 7/2005 | Stecker et al. ................... 607/55 |
| 2004/0133250 A1 * | 7/2004 | Ball et al. ......................... 607/57 |
| 2004/0225336 A1 | 11/2004 | Milojevic et al. |
| 2005/0101878 A1 | 5/2005 | Daly et al. |
| 2005/0245991 A1 | 11/2005 | Faltys et al. |
| 2005/0256561 A1 | 11/2005 | Gantz et al. |
| 2006/0287690 A1 | 12/2006 | Bouchataoui et al. |
| 2007/0179566 A1 | 8/2007 | Gantz et al. |
| 2007/0203557 A1 | 8/2007 | Gantz et al. |

FOREIGN PATENT DOCUMENTS

| | | |
|---|---|---|
| AU | 2005203696 | 11/2005 |
| WO | 96/31087 | 10/1996 |
| WO | 97/26943 | 7/1997 |
| WO | 00/69513 | 11/2000 |
| WO | 00/71063 | 11/2000 |
| WO | WO 02/082982 | 10/2002 |
| WO | 2004/004413 | 1/2004 |

OTHER PUBLICATIONS

International Preliminary Examination Report for PCT/AU03/00828 dated Oct. 8, 2004.

International Search Report for PCT/AU03/00828 dated Sep. 2, 2003.

Written Opinion for PCT/AU03/00828 dated Oct. 16, 2003.

* cited by examiner

COCHLEAR IMPLANT FITTING

This application claims the benefit of Australian Provisional Patent Application No. 2004902462, entitled "Cochlear Implant Fitting," filed on May 10, 2004, the entire disclosure and contents are hereby incorporated by reference herein.

BACKGROUND

1. Field of the Invention

The present invention relates to fitting of cochlear implants, and in particular to an electrode array fitting which allows the auditory nerve to be stimulated by both acoustic and electrical stimuli.

2. Related Art

Cochlear implants have been developed to assist people who are profoundly deaf or severely hearing impaired, by enabling them to experience a hearing sensation representative of the natural hearing sensation. For most such individuals the hair cells in the cochlea, which normally function to transduce acoustic signals into nerve impulses which are interpreted by the brain as sound, are absent or have been partially or completely destroyed. The cochlear implant therefore bypasses the hair cells to directly deliver electrical stimulation to the auditory nerve with this electrical stimulation being representative of the sound.

Cochlear implants have traditionally consisted of two parts, an external speech processor unit and an implanted receiver/stimulator unit. The external speech processor unit has been worn on the body of the user and its main purpose has been to detect the external sound using a microphone and convert the detected sound into a coded signal through an appropriate speech processing strategy.

This coded signal is then sent to the receiver/stimulator unit which is implanted in the mastoid bone of the user, via a transcutaneous link. The receiver/stimulator unit processes the coded signal into a series of stimulation sequences which are then applied directly to the auditory nerve via a series or an array of electrodes positioned within the cochlea, proximal to the modiolus of the cochlea. One such cochlear implant is set out in U.S. Pat. No. 4,532,930, the contents of which are incorporated herein by reference.

With improvements in technology it is possible that the external speech processor and implanted stimulator unit may be combined to produce a totally implantable cochlear implant unit that is capable of operating, at least for a period of time, without the need for any external device. In such a device, a microphone would be implanted within the body of the user, for example in the ear canal or within the stimulator unit, and sounds would be detected and directly processed by a speech processor within the stimulator unit, with the subsequent stimulation signals delivered without the need for any transcutaneous transmission of signals. Such a device would, however, still have the capability to communicate with an external device when necessary, particularly for program upgrades and/or implant interrogation, and if the operating parameters of the device required alteration.

Much effort has gone into developing stimulation strategies to provide for device customisation in order to produce the best available percepts for the prosthesis recipient. Nevertheless it is acknowledged in the cochlear implant field that the percepts produced by pulsatile electrical stimulation often sound unnatural and somewhat harsh. Although many patients adapt to this sound and, after some time, even find it natural, this is not always the case and some patients may experience difficulties. In some instances in the past, for potential implant recipients having some amount of residual natural hearing, the expectation of harsh and/or unnatural sounding percepts produced by cochlear implants has been less attractive than simply persisting with unassisted residual hearing.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

According to a first aspect, the present invention provides a method of fitting a cochlear prosthesis to a cochlea having residual acoustic hearing capability, the method comprising:
   determining a portion of the cochlea having residual acoustic hearing capability; and
   providing active electrodes for electrical stimulation of the cochlea adjacent only those portions of the cochlea lacking acoustic hearing capability.

According to a second aspect, the present invention provides a method of surgically implanting an electrode array of a cochlear prosthesis to a cochlea having residual acoustic hearing capability, the method comprising:
   determining an apical portion of the cochlea having residual acoustic hearing capability; and
   introducing the electrode array to the cochlea from the basal end of the cochlea, to position the array such that active electrodes are provided adjacent a basal portion of the cochlea, and such that the array does not extend to be adjacent the apical portion of the cochlea.

According to a third aspect, the present invention provides a method of determining a patient map for controlling application of multi-electrode stimulations to a cochlea having residual acoustic hearing capability, the method comprising:
   determining an apical portion of the cochlea having residual acoustic hearing capability; and
   defining the patient map so as to prevent application of stimuli by electrodes adjacent to the apical portion of the cochlea.

According to a fourth aspect the present invention provides a cochlear prosthesis comprising a storage means storing a patient map for controlling application of electrical stimuli by an electrode array of the cochlear prosthesis to the cochlea of a recipient of the cochlear prosthesis, wherein the patient map is configured to prevent application of stimuli to a portion of the recipient's cochlea having residual acoustic hearing capability.

According to a fifth aspect the present invention provides a cochlear prosthesis comprising
   an electrode array for application of electrical stimuli to a recipient's cochlea;
   an acoustic transponder for application of acoustic signals to the recipient's ear;
   a processor for processing a detected sound signal to produce signals defining multi-channel electrical stimuli for application by the electrode array to a portion of a recipient's cochlea lacking acoustic hearing capability, and for processing the detected sound signal to produce an amplified signal for application by the acoustic transponder.

According to a sixth aspect the present invention provides a speech processor for a cochlear implant, the speech processor comprising a storage means storing a patient map for controlling application of electrical stimuli by an electrode array of the cochlear prosthesis to the cochlea of a recipient of the cochlear prosthesis, wherein the patient map is configured to prevent application of stimuli to a portion of the recipient's cochlea having residual acoustic hearing capability.

According to a seventh aspect the present invention provides a speech processor for a cochlear prosthesis, the speech processor comprising:
   means for processing a detected sound signal to produce signals defining multi-channel electrical stimuli for application by an electrode array to a portion of a recipient's cochlea having incomplete acoustic hearing capability; and
   means for processing the detected sound signal to produce an amplified signal for acoustic application to the recipient's ear.

According to an eighth aspect the present invention provides a computer program for facilitating surgical implantation of an electrode array of a cochlear prosthesis to a cochlea having residual acoustic hearing capability, the computer program comprising:
   code for generating instructions defining an acoustic signal to be intra-operatively applied to the cochlea;
   code for obtaining telemetry data from a sense electrode of the electrode array indicating a neural response evoked by the acoustic signal; and
   code for determining an apical portion of the cochlea having residual acoustic hearing capability.

According to a ninth aspect the present invention provides a computer program for generating a patient map for controlling application of multi-electrode stimulations to a cochlea having residual acoustic hearing capability, the computer program comprising:
   code for determining an apical portion of the cochlea having residual acoustic hearing capability; and
   code for defining the patient map so as to prevent application of stimuli by electrodes adjacent to the apical portion of the cochlea.

According to a tenth aspect the present invention provides a computer readable medium having recorded thereon a computer program in accordance with the eighth aspect or ninth aspect.

According to an eleventh aspect the present invention provides a method of fitting a cochlear implant to a cochlea, comprising:
   implanting an electrode array having a first plurality of electrodes;
   determining an apical portion of the cochlea having residual acoustic hearing capability; and
   mapping to a subset of the first plurality of electrodes a second plurality of electrical signal channels for application to the cochlea, to supplement the residual acoustic hearing capability of the cochlea, the second plurality being less than the first plurality.

BRIEF DESCRIPTION OF THE DRAWINGS

By way of example only, preferred embodiments of the invention will be described with reference to the accompanying drawings, in which:

FIG. 2b is a flowchart illustrating the intra-operative process of FIG. 2a;

FIG. 3b is a flowchart illustrating the post-operative process of FIG. 3a;

DETAILED DESCRIPTION

Figure 1:
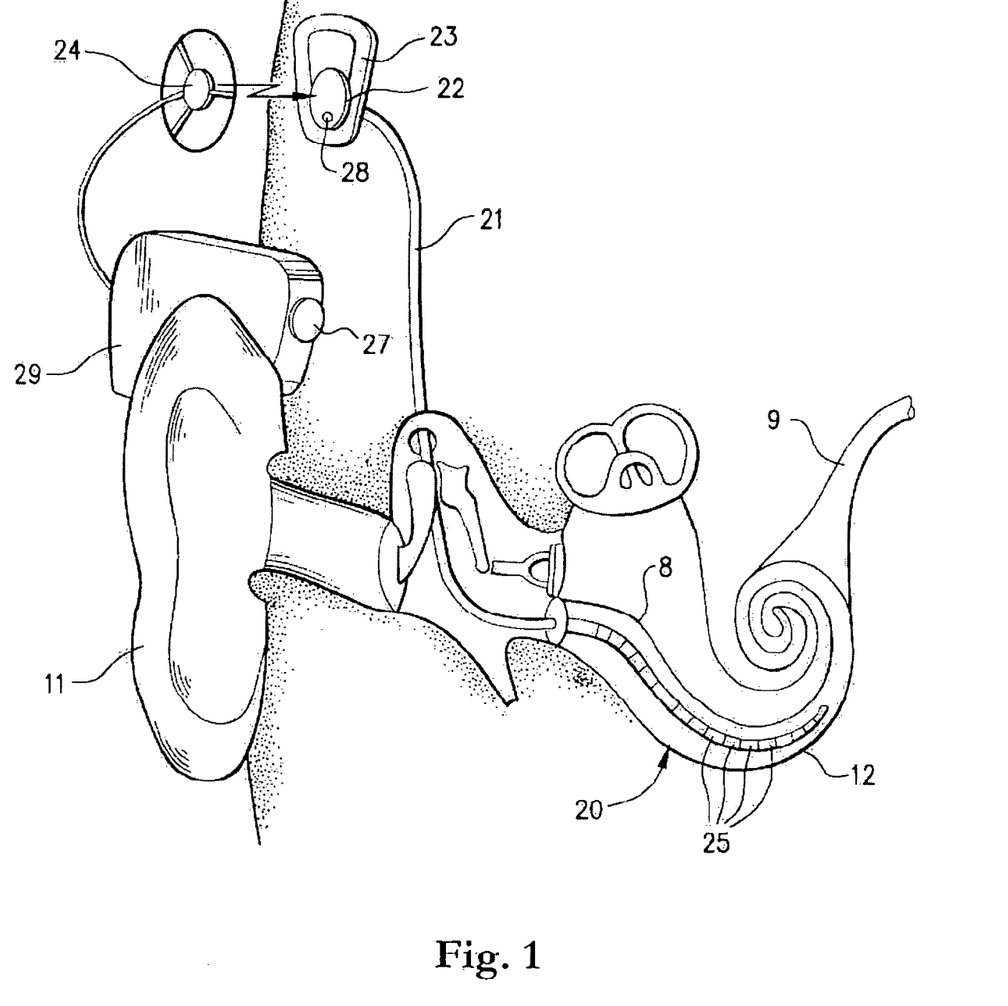
FIG. 1 is a pictorial representation of a cochlear implant system.

Before describing the features of the present invention, it is appropriate to briefly describe the construction of a cochlear implant system with reference to FIG. 1.

Cochlear implants typically consist of two main components, an external component including a sound processor 29, and an internal component including an implanted receiver and stimulator unit 22. The external component includes an on-board microphone 27. The sound processor 29 is, in this illustration, constructed and arranged so that it can fit behind the outer ear 11. Alternative versions may be worn on the body or it may be possible to provide a fully implantable system which incorporates the speech processor and/or microphone into the implanted stimulator unit. Attached to the sound processor 29 is a transmitter coil 24 which transmits electrical signals to the implanted unit 22 via an RF link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. While the cochlea is generally spiral shaped as shown, it is convenient to describe electrode positions and the like as being "along" the cochlea between a basal end of the cochlea and an apical end of the cochlea as if the cochlea were unrolled to lie straight. The operation of such a device is described, for example, in U.S. Pat. No. 4,532,930.

The sound processor 29 of the cochlear implant can perform an audio spectral analysis of the acoustic signals and outputs channel amplitude levels. The sound processor 29 can also sort the outputs in order of magnitude, or flag the spectral maxima as used in the SPEAK strategy developed by Cochlear Ltd.

With the continued improvement in performance of Cochlear implants, more recipients receiving implants have appreciable residual hearing capability. The present invention provides for bimodal stimulation of the cochlea by electrical and acoustic stimulation, to take advantage of the recipient's residual natural hearing capability, while supplementing that natural hearing with electrical stimuli to convey sound information which is only partially conveyed or is not conveyed by the natural hearing of the recipient. The bimodal stimulation may be controlled by a speech processor having the ability to process a detected sound to produce both electrical stimulations for application by an electrode array and acoustic stimulations for application by a hearing aid. Alternatively, a speech processor for producing electrical stimulations may be used alone, without generation of any acoustic stimulation beyond that naturally entering the ear. Alternatively, a first speech processor for generating electrical stimulations may be used in conjunction with a second speech processor for producing acoustic stimulations.

In implementing the present invention, it is desirable to implant the electrode array without affecting the residual hearing, whether by adversely influencing the fluid dynamics of the inner ear or damaging inner ear structures. The risk of such damage, and in particular the likelihood of perforation of the basilar membrane which would destroy all remaining hearing, increases with insertion depth of the electrode array. Damage to the lateral or modiolar wall of the cochlea may also occur during implantation. Thus a partial insertion of the array leads to a lower risk of such damage. On the other hand, use of suitable surgical implantation techniques and suitable electrode arrays may enable complete insertion with an acceptable risk of such damage, in accordance with the third aspect of the invention.

Further, it is desirable to optimize the combination of electrical and acoustical stimulation in the fitting process, whether intra-operatively in the positioning of the electrode array, or post-operatively in establishing an optimal patient map, or both. It may further be necessary to determine which electrodes are to be active and which are to remain inactive, and to determine the frequency allocation of each active electrode so as to optimize the combinatory hearing.

The present invention further recognises that the recipient's residual hearing capability can be assessed objectively without requiring subjective patient responses, by detecting a neural response evoked by acoustic and/or electrical stimulation. For instance, an electrode of the electrode array may be used as a sense electrode for sensing an evoked neural response. The sensing of the evoked neural response is preferably performed in accordance with the method set out in International Patent Publication Number WO 02/082,982, the contents of which are incorporated herein by reference. By thus eliminating the need for subjective patient responses in determining a residual hearing capability, the present invention enables intra-operative determination of residual hearing, thus providing for the ability to intra-operatively determine optimal insertion depth or position of the electrode array. Further, measurement of the evoked neural response can be used to objectively post-operatively optimise the electrode mapping configuration for each electrode position along the cochlea, for a recipient with residual hearing.

Such embodiments of the present invention also recognize the difficulty in precisely mapping a particular frequency to a position on the cochlea corresponding to that frequency. That is, it is difficult to accurately define an appropriate insertion depth for a partial insertion of an electrode array based on a previously measured audiogram of the cochlea. Further, it is difficult to know an actual depth to which an array has been inserted, even when imaging the array and cochlea during insertion, for example by X-ray.

Similarly, once an array is inserted, whether partially or fully, it is difficult to accurately map frequency bands to electrodes to correspond to a position of each electrode along the cochlea. This problem is compounded by the fact that an acoustic stimulation position for a particular frequency may not necessarily correspond to an appropriate electrical stimulation position for that frequency. Incorrect array positioning and/or incorrect frequency allocation to electrodes will lead to shifted frequency delivery to the cochlea, and can lead to contraposition of the acoustically delivered frequency range against the electrically delivered frequency range.

However, by sensing the evoked neural response, such embodiments of the invention enable such frequency vs. position determinations to be carried out with reference to an actual position of the sense electrode.

Such objective measurement of the residual hearing capability of the cochlea may further be particularly advantageous where the recipient is a young child unable to indicate subjective responses to auditory stimuli, and thus unable to assist in measurement of an audiogram. A cut-off frequency at the limit of the residual hearing is preferably also determined with reference to objective neural measurements rather than a subjective audiogram. One reason to prefer subjective measurement of the cut-off frequency is that the limited frequency resolution of a partially damaged cochlea raises the possibility that a stimuli of a first frequency will produce a subjective response in the patient, but only because that frequency raises a neural response in auditory nerves which are typically considered to relate to a different (usually lower) frequency. In such circumstances, the auditory nerve relating to the first frequency may be inoperable, yet stimulation at that frequency causes a subjective response, which may lead to an incorrect conclusion that the auditory nerves relating to the first frequency are operable. To the contrary, an objective interactive measurement of a neural response may avoid this problem. Additionally or alternatively, use of the TEN test developed by Moore et al (Moore, B. C. J., Glasberg, B. R., Stone, M. A., 2004. *A new version of the TEN test with calibrations in dB* HL. Ear Hear. 25, 478-487) may be used to accurately measure the position of residual hearing in the cochlea.

To obtain a detailed impression of the residual hearing capability of the cochlea and of how electrical and acoustic stimulation will interact, several measurements of the neural response are preferably obtained. To address the localised sensitivity of the cochlea to electrical stimuli, the neural response evoked by an electrical stimulus at a specific location along the cochlea is preferably obtained, for a plurality of positions along the cochlea. Further, the neural response evoked by acoustic stimulation at specific frequencies is preferably determined by applying an acoustic stimulus of specific frequency and using an electrode in a position tonotopically corresponding to that frequency to measure the neural response evoked by the acoustic stimulation, for a plurality of frequencies in the range audible to normal hearing. Additionally, the interaction between acoustic stimuli and electrical stimuli is preferably assessed by recording electrically evoked compound action potentials in the presence of acoustic masker stimuli, and also recording acoustically evoked compound action potentials in the presence of electrical masker stimuli. An appropriate electrical masker stimuli may comprise a forward masking paradigm, with a burst of electrical masker preceding the acoustical signal. An electrical masker stimuli may comprise a pulse burst at a rate equal to the mapping rate on a single electrode. An acoustic masker stimuli may comprise broadband or narrowband noise at high levels, with narrowband noise suitable for investigating tonotopic (frequency to location) characteristics of the cochlea.

The amplitude of compound action potentials produced by acoustic stimuli and electrical stimuli are around the same order of magnitude and thus interfere in a measurable way.

To provide for such measurements, a system could be used comprising a cochlear implant with neural response measurement and recordal capabilities, software to drive appropriate stimulus and measurement procedures, and an acoustic stimulator.

Figure 2A:
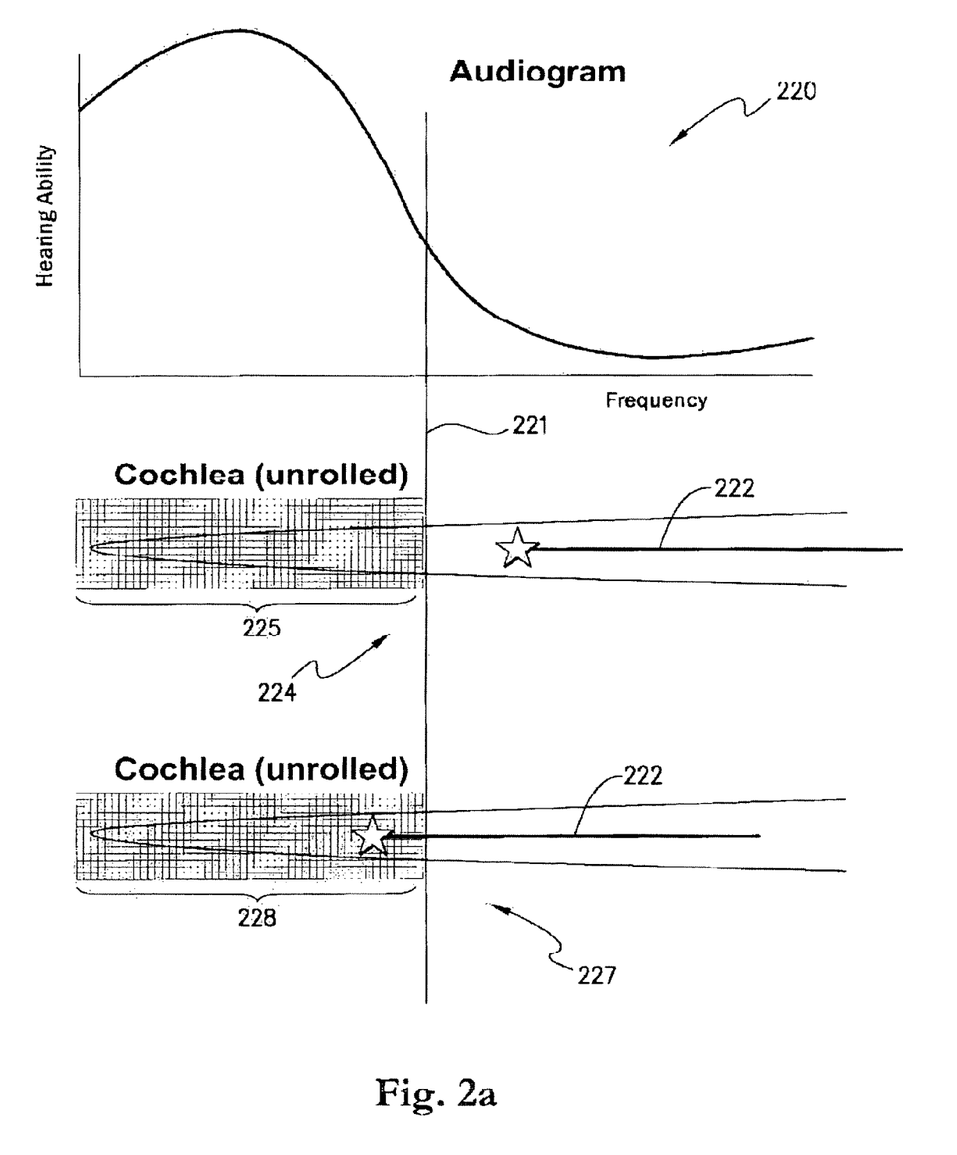
FIG. 2a is a schematic drawing of an implementation of intra-operative determination of insertion depth of an electrode array to a cochlea having residual acoustic hearing capability.
Figure 2B:
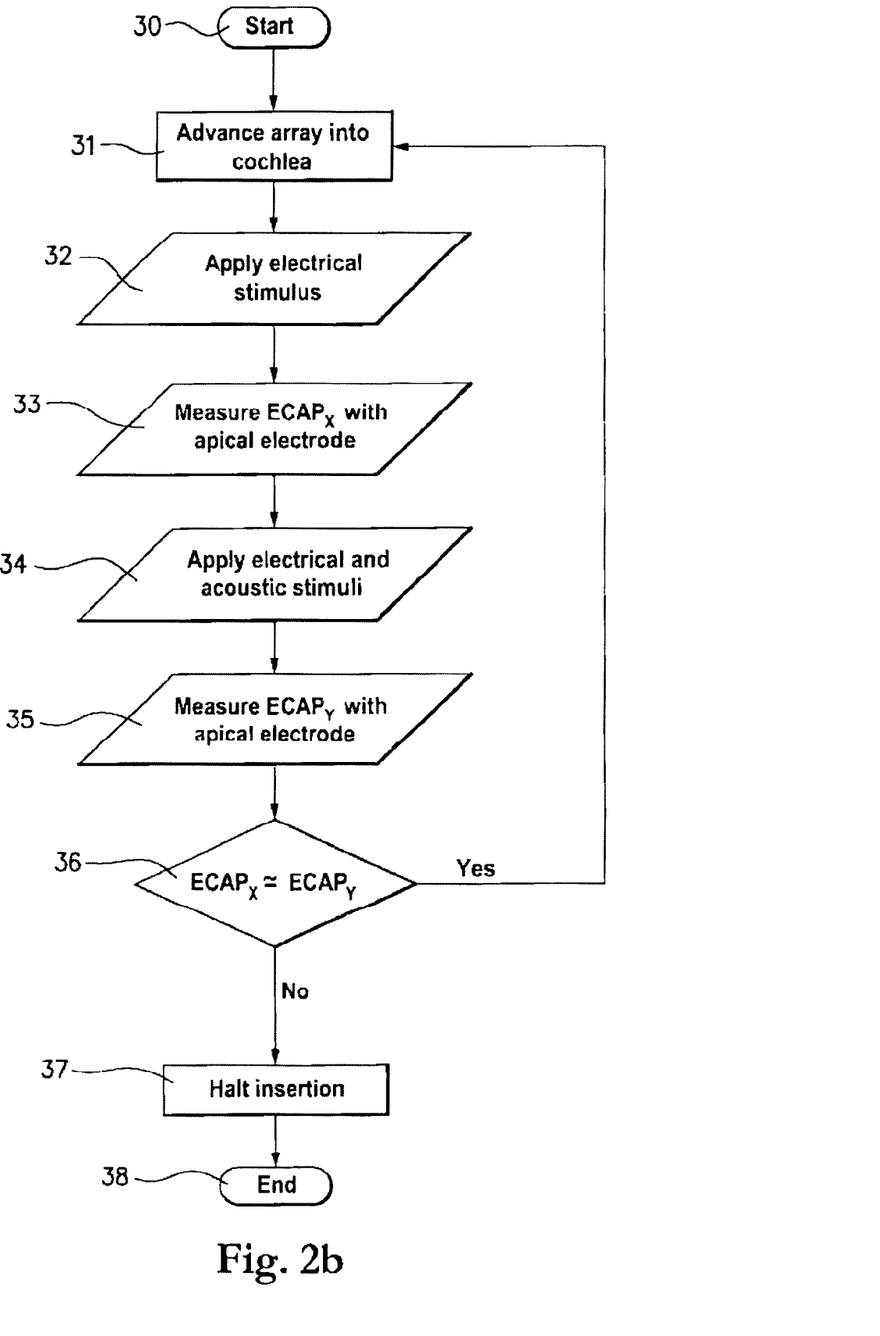

A first embodiment of the invention is illustrated in FIGS. 2a and 2b. In this embodiment, the method of the present invention is used to intra-operatively determine an optimal insertion depth of an electrode array. In patients with residual hearing it is difficult to determine a suitable depth of insertion of the electrode array, due to difficulties in precisely determining the location of the electrode, or in precisely determining the location of surviving neural elements that still can respond to acoustical stimulation. In this embodiment, since residual hearing usually exists on the more apical (lower frequency) part of the cochlea; the electrode array is introduced only until the point where usable hearing begins. An advantage of this technique is that trauma is reduced to a minimum, and that the cochlear mechanics (especially at the point where residual hearing is present) are influenced as little as possible. That is, no portion of the electrode array is positioned adjacent to the apical portion of the cochlea having residual acoustic hearing capability, and the array is thus less likely to interfere with or damage the residual acoustic hearing ability of that portion of the cochlea, while providing electrical stimulation to the basal portion of the cochlea lacking in acoustic hearing capability. Accordingly, surgical trauma to the apical portion of the cochlea may be avoided or minimized by this method.

The optimal insertion depth is determined intra-operatively during the insertion of the electrode array, by investigating the interaction between electrically evoked and acoustically evoked neural responses locally at the point of insertion of the tip of the electrode array. The electrode array is advanced by increments into the cochlea, with the interaction being determined after each incremental advance. When an increase of the interaction strength is determined the insertion is halted, or the electrode may be slightly withdrawn, as the electrode tip has then reached a point where residual hearing exists.

In the present embodiment, the interaction between the electrical and acoustical interaction is evaluated as follows. Initially, the most apical electrode records a first compound action potential evoked by application of an electrical stimulus of a given amplitude. The most apical electrode is then used to record a second compound action potential evoked by application of an essentially identical electrical stimulus of the same amplitude, in the presence of a background acoustic noise, preferably a narrowband background acoustic stimulus of a frequency substantially corresponding to the position of the tip electrode, applied to the cochlea. Should the first recorded ECAP and the second recorded ECAP be substantially identical, it can be assumed that the apical electrode of the array is yet to reach the residual functional 'normal hearing' part of the cochlea. However, should the first recorded ECAP and the second recorded ECAP substantially differ, this gives an indication that the presence of masking acoustic noise is evoking a component of neural response which interferes with that evoked by the electrical stimulus. Accordingly, the portion of the cochlea proximal to the apical electrode exhibits residual acoustic hearing capability.

This procedure is schematically indicated in FIG. 2a. At 220, the recipient's audiogram is displayed, with considerable residual acoustic hearing capability evident in the low frequencies. A cut-off frequency for useful hearing is indicated at 221, which also marks the place in the unrolled cochlea diagrams 224, 277 where residual hearing terminates. In the unrolled cochlea, the area 225, 228 of the cochlea that can be measurably masked by a broadband acoustical masking stimulation is indicated by a hashed background. If the electrode array 222 is inserted with the tip in the deaf part of the cochlea (cochlea diagram 224) and an ECAP is recorded at the apical electrode with and without a background acoustical masker, no difference in ECAP amplitude is expected. However, when the electrode array tip is introduced into the acoustically maskable region 228 (corresponding to the region containing residual hearing), as shown in cochlea diagram 227, the ECAP amplitude with a background acoustical masker present decreases as compared to the unmasked NRT.

FIG. 2b is a flowchart of the intra-operative process illustrated in FIG. 2a. At 30 the process commences, after which the electrode array is incrementally advanced by a small amount into the cochlea at 31. An electrical stimulus is then applied at 32 in the absence of acoustic stimulation, and a first ECAP denoted $ECAP_x$ is recorded at 33 using the apical electrode of the array. Subsequently, another electrical stimulus substantially identical to the first stimulus is applied at 34 simultaneously with an acoustical masking stimulation. The apical electrode is again used at 35 to measure a second ECAP, denoted $ECAP_y$. At 36 a comparison is made between $ECAP_x$ and $ECAP_y$. Should $ECAP_x$ be substantially identical to $ECAP_y$, this indicates that the presence of the acoustic masking signal has made no measurable difference to the evoked neural response, thus indicating that there exists no residual acoustic hearing capability at the current position of the apical electrode. Accordingly, the process returns to 31 at which the electrode array is again incrementally advanced into the cochlea and the process is repeated to determine whether residual acoustic hearing capability exists at the new location of the apical electrode. Should $ECAP_x$ be different to $ECAP_y$, this indicates that the presence of the acoustic masking signal has made a difference to the evoked neural response, thus indicating that residual acoustic hearing capability exists at the present position of the apical electrode. Accordingly, at 37 the insertion is halted and the process ends at 38.

In addition to merely determining a point at which residual acoustic hearing capability commences, the process may further include assessing a relative strength of the acoustic hearing capability beyond the threshold, by further inserting the electrode array during the operation for such assessment, and withdrawing the array to its desired post operative position prior to the conclusion of the operation.

In a preferred embodiment the electrode array has a number of electrodes which is significantly greater than the number of channels to be applied by the speech processing scheme to be implemented by the speech processor. Such an electrode is set out in International Publication No. WO 03/003791, the contents of which are incorporated herein by reference. Providing an increased number of electrodes from which to choose for use in applying each signal channel recognises that, depending on the surgical implantation process, some of the electrodes may be positioned adjacent the apical portion of the cochlea and thus may be inactivated, and/or some of the electrodes may be positioned outside the basal end of the cochlea. Providing an electrode array with sufficiently many electrodes ensures that a sufficient number of the electrodes are adjacent that portion of the cochlea which lacks adequate residual acoustic hearing capability. Such embodiments cater for the application of, for example, all 22 signal channels of an ACE speech processing scheme to only that portion of the cochlea which lacks adequate residual acoustic hearing capability, and provide for finer frequency resolution between signal channels over that portion of the cochlea. To enable such fine frequency resolution, the speech processing scheme implemented is preferably applied to a subset of the audible frequency range tonotopically corresponding to the portion of the cochlea lacking adequate residual acoustic hearing capability.

Alternatively, once a suitable depth of insertion has been determined, a selection may be made of a suitable length electrode to implant. That is, the electrode used for the above determination of suitable insertion depth may be withdrawn, and an electrode of suitable length may be selected and then implanted to the appropriate insertion depth to conclude the surgical procedure. However, care must be taken to avoid or limit damage to the cochlea during such an operative procedure.

Once such partial insertion is complete, a patient map should be determined to allocate suitable frequencies and amplitudes (i.e. C and T levels) to each electrode of the partially inserted array. In particular, in allocating frequency bands to electrodes in the patient map, it is desirable to avoid: (a) the tip electrode(s) applying frequencies which are heard naturally in the more apical part of the cochlea (potentially leading to a "duplicate perception" at that frequency); or (b) the tip electrode frequency being too high and leaving a frequency "gap" which is neither heard naturally nor conveyed electrically.

Figure 3A:
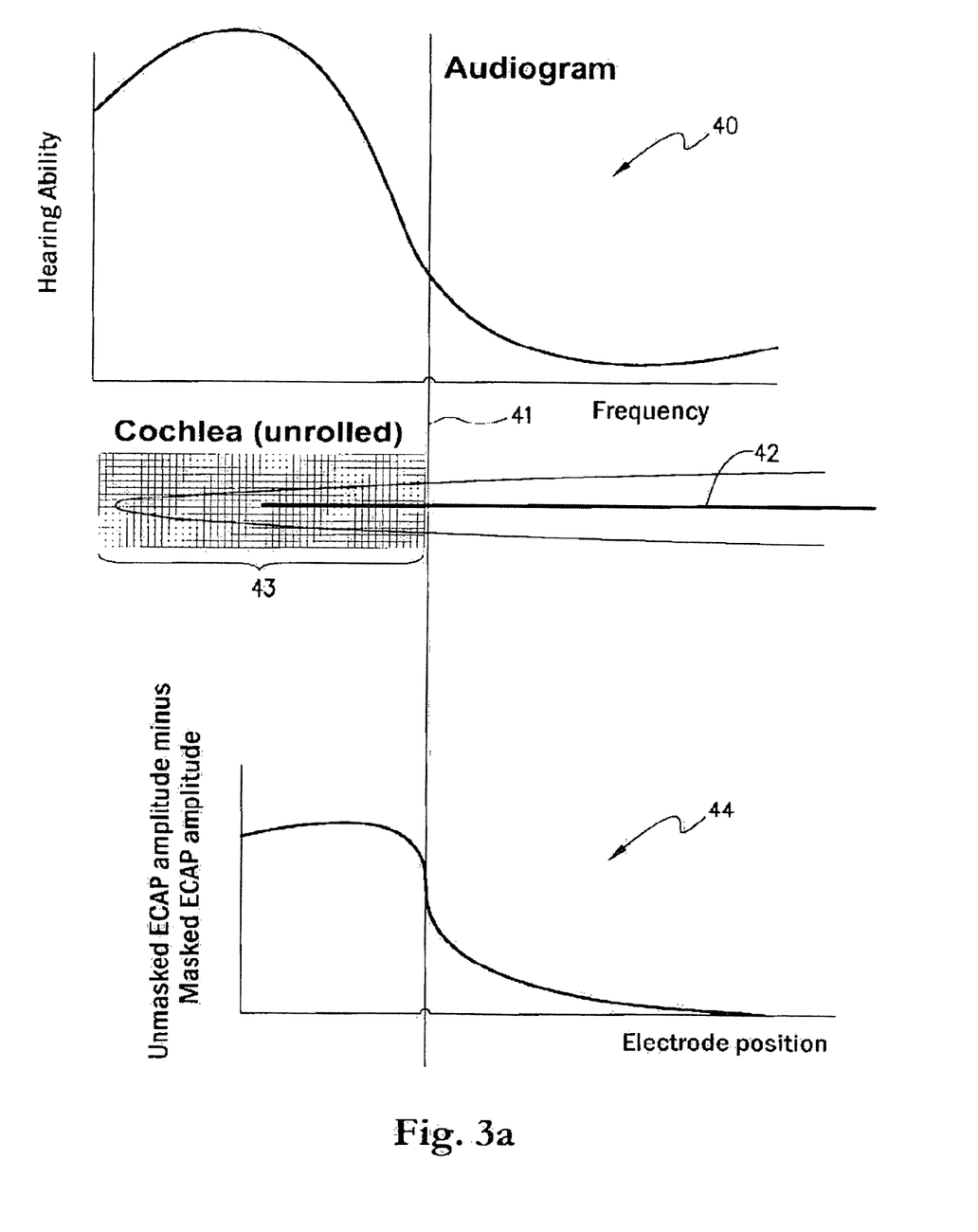
FIG. 3a is a schematic drawing of post operative determination of a patient map for a cochlea having residual acoustic hearing capability.

FIG. 3a illustrates a second embodiment of the present invention, in which the electrode array 42 is inserted fully within the cochlea, and involving a post-operative decision as to which electrodes to inactivate and which to include in the patient map. At 40 the residual hearing capability of the recipient is illustrated, indicating significant residual hearing at low frequencies, up to a threshold 41. Threshold 41 also indicates a position along the cochlea at which the residual hearing portion 43 terminates. In this embodiment, only a subset of electrodes are active in the map. Thus the natural pathway for delivery of acoustic sound is utilised to the extent that it still exists, while electrical stimuli are provided to convey sound information which is no longer perceptible by the cochlea and/or to supplement sound information only partially perceptible by the cochlea. Accordingly, the implant recipient will receive natural sounding percepts from those portions of the cochlea having hearing capability. This technique is advantageous in that when the hearing loss progresses over time, the patient map can be adjusted accordingly, without the need for further surgical intervention.

However, once again, in order to determine an optimal patient map it is desirable to assess the interaction between electrical and acoustic stimulation along the cochlea, in order to determine the physical point 41 in the cochlea at which electrical stimulation begins to interfere with (useful) acoustical stimulation.

Figure 3B:
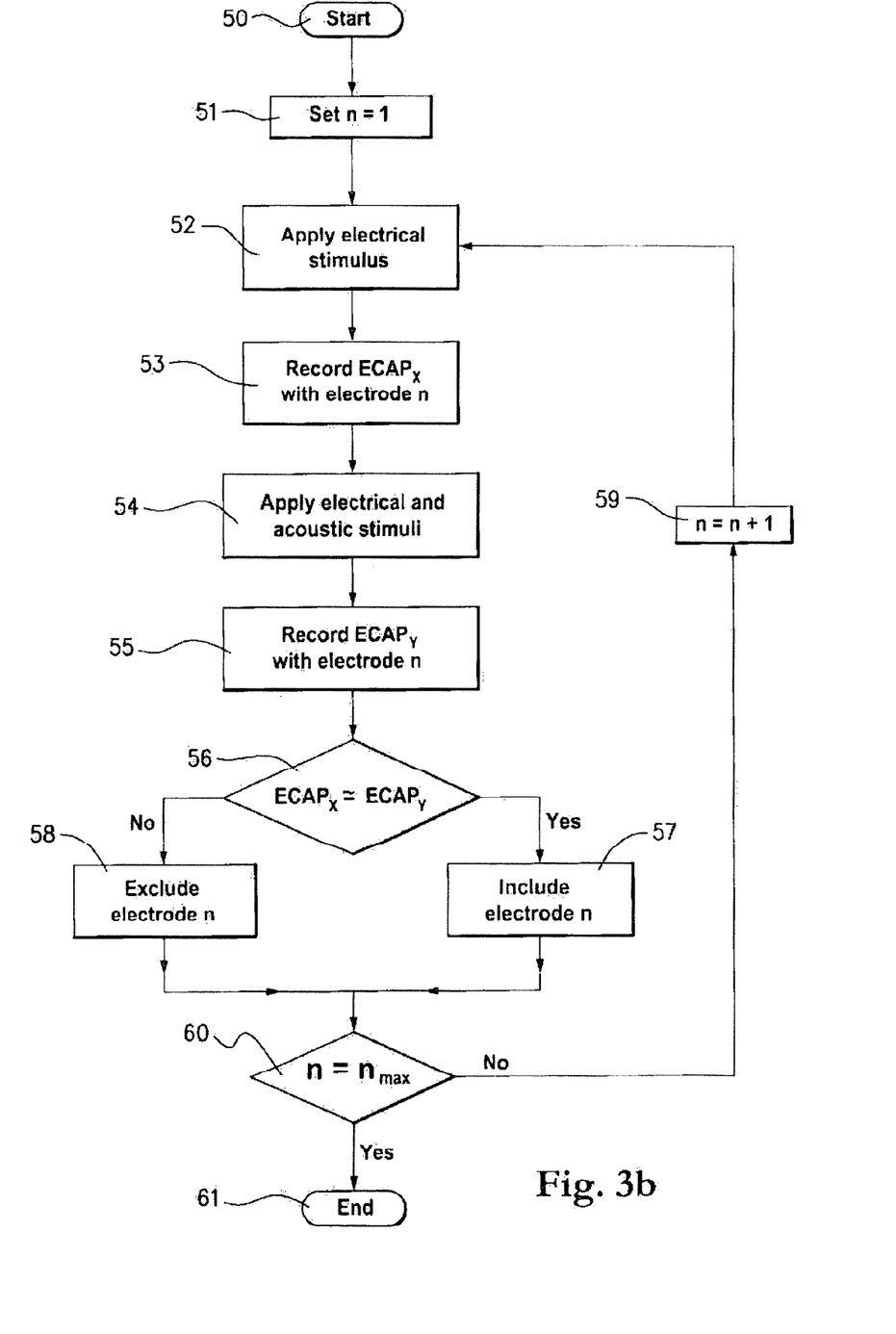

FIG. 3b is a flowchart illustrating a process for determining a suitable patient map for the implant configuration set out in FIG. 3a. At 50 the process begins, and at 51 a sense electrode is set to be a first electrode of the array. At 52 an electrical stimulus is applied in the absence of any acoustic stimulation, and at 53 the first electrode is used to sense and record a first ECAP, denoted $ECAP_x$, evoked by the electrical stimulus applied at 52.

Subsequently, at 54 a substantially identical electrical stimulus is applied, and in addition a simultaneous acoustic stimulus is applied having at least a frequency component tonotopically corresponding to the position of electrode n. At 55 the same (first) electrode is used to sense and record a second ECAP, denoted $ECAP_y$, evoked by the simultaneous electrical and acoustic stimuli applied at 54.

A comparison is then made at 56 of $ECAP_x$ and $ECAP_y$. Should $ECAP_x$ be substantially identical to $ECAP_y$, as shown in FIG. 3b, then this indicates that the presence or absence of acoustic stimulation has made no measurable difference, and thus indicates that residual hearing capability does not exist proximal to the first electrode. In this event the first electrode is at 57 included in the patient map in order that the first electrode is used to apply electrical stimuli to the cochlea to convey sound information tonotopically corresponding to the position of that electrode, due to the natural hearing no longer conveying such sound information. Alternatively, should the comparison made at 56 reveal that $ECAP_x$ is not substantially identical to $ECAP_y$, then this indicates that the presence of the acoustic masking stimulus has made a difference to the evoked neural response, thus indicating that residual acoustic hearing capability exists proximal to the first electrode. In this event, electrode n (n=1) is excluded from the patient map at 58. This process is repeated for all electrodes of the array by incrementing n at 59, unless all electrodes have been assessed, in which case $n=n_{max}$ and decision 60 causes the process to end at 61.

It is to be appreciated that the interaction between electrical and acoustic stimuli may be assessed in an alternate manner. For instance, the interaction may alternatively or additionally be assessed by applying a narrowband acoustic stimulus and recording an evoked CAP using a sense electrode tonotopically corresponding to the frequency of the narrowband stimulus. Then a substantially identical narrowband acoustic stimulus may be applied simultaneously with a masking electrical stimulation (for example applied by an electrode adjacent to the sense electrode), and again recording an evoked CAP. This process may be repeated for acoustically applied frequencies throughout the normal hearing range with a tonotopically corresponding sense electrode for each frequency.

Once an assessment has been made of the interaction between acoustic and electrical stimuli along the cochlea an "interaction map" of the cochlea may be produced, of the type illustrated by audiogram 44 in FIG. 3a. Such an interaction map may be used in conjunction with conventional audiometry to determine a suitable cut off frequency 41, to determine where in the cochlea electrical stimulation does not influence the acoustic hearing capability, to map the processor on the non interacting electrodes only, using a frequency allocation table (FAT) that only stimulates those frequencies that are not represented and conveyed by the auditory system naturally.

The audiogram shown in FIG. 3a is representative of the most common type of hearing loss in which a cochlea loses hearing ability at high frequencies. However it is to be appreciated that, for a cochlea where hearing capability is deficient in alternate ways, such as the loss of low frequency capability, the embodiment of FIGS. 3a and 3b can still be used to provide for electrical supplementation of residual acoustic hearing capability, wherever that capability may exist in the operating frequency range.

Figure 4:
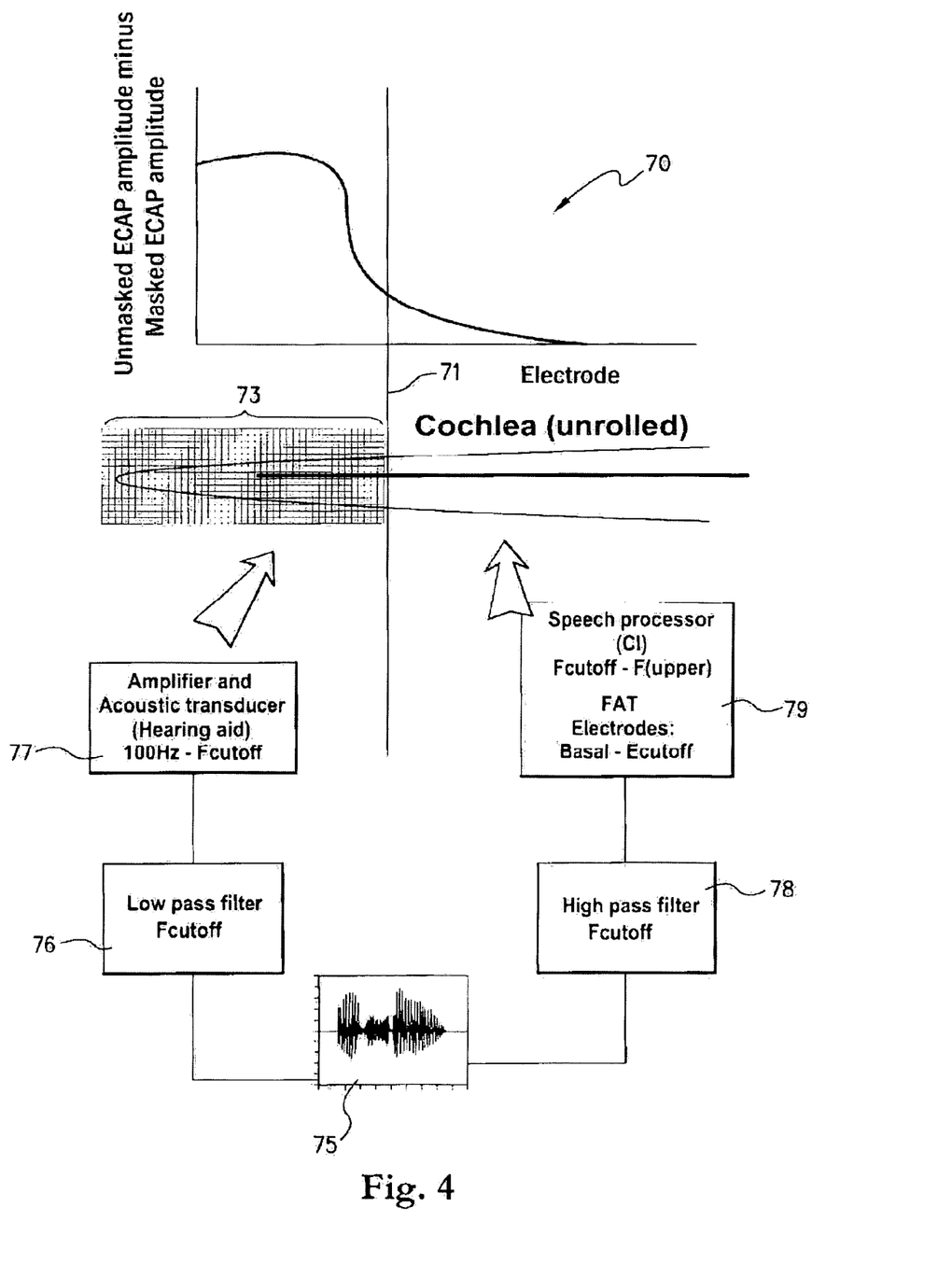
FIG. 4 is a schematic drawing of mapping a device using both electrical and acoustic modes of stimulation.

The embodiments shown in FIGS. 2a, 2b and FIGS. 3a, 3b may each be incorporated into a bimodal device. Illustrated in FIG. 4 is a bimodal device based on the embodiment of FIGS. 3a, 3b. Once the cut off frequency 71 (corresponding to a "cut-off electrode") has been determined, whether by the method set out in FIG. 2b or FIG. 3b, electrical stimuli may be applied in one mode above that frequency, and acoustic stimuli may be applied in the other mode below that frequency. At 70 the determined masking profile is displayed. Portion 73 of the cochlea is where residual acoustic hearing capability exists. Knowing the acoustic cut off frequency of that residual hearing, and knowing which electrode is located at the cut off boundary 71 in the cochlea, it is possible to separate detected sound 75 into 2 components. Below the cut-off frequency the sound is amplified and applied to the ear acoustically, by low pass filter 76 and transducer 77. The portion of the detected sound above the cut off frequency is processed by a high pass filter 78 and a cochlear implant speech processor 79 and mapped to those electrodes that are in the non-functional part of the cochlea. In this way the accessible frequency range is optimised, and the interaction between acoustic and electric hearing is minimized.

It is to be appreciated that electrical stimulation may also be used to supplement the application of acoustic stimulation to the portion 73 of the cochlea having partial residual hearing. Such supplemented electrical stimulation may be mapped to have a strength to complement the residual audiogram strength along the cochlea in region 73. Such embodiments provide for a transition from purely acoustic hearing at the apical end of the cochlea to purely electrical stimulation at the basal end of the cochlea, with a central portion of the cochlea having both acoustic and electrical stimulation applied thereto and the central portion of the cochlea being relied upon to convey both acoustic and electrical stimulation. Should the residual hearing be inadequate, electrical stimulation may be applied by all electrodes of the array, with apical electrodes being mapped to have a strength which complements the residual acoustic hearing strength of the portion 73 of the cochlea.

Further, high pass filter 78 may be excluded where an appropriate patient map exists in speech processor 79 which inactivates apical electrodes of the array.

A system for clinical testing and/or fitting of a cochlear implant to be used to supplement the residual acoustic hearing capability of a cochlea is disclosed. A trigger signal is applied electrically via the electrode array of the cochlear implant and acoustically via headphones. The trigger signal is generated by a personal computer (PC) with infrared connection via L34, a digital to analogue converter and a clinical audiometer to the headphones, and via L34, PCI and a Sprint speech processor to the cochlear implant. The PC-infrared-L34-DAC connection may alternatively be provided by a triggerable signal generator with analogue output. For example, the system may be used in obtaining intra-operative NRT recordings of both electrical and acoustic stimuli to determine suitable array insertion depths.

The system may further be used to determine suitable delays to be introduced in order to ensure accurate timing of the delivery of electrical stimulations relative to acoustic stimulations. Such an embodiment recognizes that, due to the differing pathways for delivery of acoustic stimuli and electric stimuli to the cochlea, neural responses caused by electrical stimuli may be mis-timed relative to neural responses caused by acoustic stimuli. In certain circumstances such a mis-timing may reduce the intelligibility of speech or otherwise have an undesirable effect on sound perception by the user. Should neural responses to acoustic stimuli arise after neural responses to electrical stimuli, for instance due to the time of transmission from the outer ear, through the middle ear, into the inner ear and via the basilar membrane, an appropriate delay in applying electrical stimulation is preferably introduced. The timing of the electrical stimulations relative to the timing of the acoustic stimulations may be optimized by use of neural response measurements, and appropriate adjustments are preferably made to the delay in delivery of electrical stimuli.

Uses of embodiments of the present invention include research and auditory states monitoring, in which a bimodal speech processor could generate an acoustical stimulus and record the resulting CAP, comparing it to previous CAP recordings. If the recipient's hearing is further deteriorating and refitting is needed, this could be detected automatically by such a system. Embodiments of the present invention may further provide for high resolution audiogram imaging in combination with classical audiometry, and may provide for detection of double peaks in the neural response.

It is to be appreciated that determination of tonotopic cochlear positions in this document is not limited to a classical determination of cochlear position relative to frequency or pitch. In particular, it is to be appreciated that existing formulae to relate cochlear position the pitch, such as Greenwood's formulae (J. Acoust. Soc. Am. Vol 87, No 6, June 1990) may not always be sufficiently accurate in relation to tonotopic cochlear positions for electrical stimuli.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of fitting a cochlear prosthesis to a cochlea having residual acoustic hearing capability, comprising:
    at least partially implanting an electrode array having one or more electrodes therein into the cochlea;
    applying stimulation to the cochlea via at least one of the one or more electrodes;
    objectively assessing the capability of one or more portions of the cochlea, to which a non-electrical stimulation has been applied, to respond to non-electrical stimulation based on a measured neural response of said one or more portions to said non-electrical stimulation; and
    positioning the electrode array in the cochlea such that at least one of said one or more electrodes is adjacent a portion of the cochlea lacking the capability to respond to non-electrical stimulation based on the measured neural response.

2. The method of claim 1, further comprising applying non-electrical stimulation in the form of acoustic stimulation to the cochlea, and measuring a neural response of said one or more portions of the cochlea to said acoustic stimulation.

3. The method of claim 1, further comprising:
    measuring said neural response of said one or more portions with at least one of said one or more electrodes.

4. The method of claim 2, wherein said measuring said neural response of said one or more portions of the cochlea to said acoustic stimulation comprises:
    measuring said neural response to said acoustic stimulation in the absence of electrical stimulation.

5. The method of claim 2, further comprising:
    applying electrical stimulation to the cochlea; and
    measuring said neural response of said one or more portions of the cochlea to said acoustic stimulation in the presence of said electrical stimulation.

6. The method of claim 1, wherein applying stimulation to the cochlea comprises applying electrical stimulation to the cochlea, and wherein the method further comprises:
    measuring a neural response of said one or more portions of the cochlea to said electrical stimulation.

7. The method of claim 6, further comprising:
    applying non-electrical stimulation in the form of acoustic stimulation to the cochlea; and
    measuring said neural response of said one or more portions of the cochlea to said electrical stimulation in the presence of said acoustic stimulation.

8. The method of claim 1, further comprising:
    stimulating said portion of the cochlea lacking the capability to respond to non-electrical stimulation with said at least one electrode so as to evoke a hearing perception; and
    substantially simultaneously applying non-electrical stimulation in the form of acoustic stimulation to the cochlea so as to evoke a hearing perception at one or more portions having the capability to respond to non-electrical stimulation.

9. A method of fitting a cochlear prosthesis to a cochlea having residual acoustic hearing capability, comprising:
 at least partially implanting an electrode array having one or more electrodes therein into the cochlea;
 applying stimulation to the cochlea via at least one of the one or more electrodes;
 objectively assessing the acoustic hearing capability of one or more portions of the cochlea based on a measured neural response of said one or more portions to said stimulation; and
 positioning the electrode array in the cochlea such that at least one of said one or more electrodes is adjacent a portion of the cochlea lacking acoustic hearing capability,
 wherein objectively determining that at least one of said one or more portions of the cochlea have acoustic hearing capability comprises approximately determining a most apical point in the cochlea lacking acoustic hearing capability, and wherein the method further comprises:
  inserting said electrode array into said cochlea such that an electrode positioned at the distal end of said electrode array is approximately adjacent said most apical point,
 wherein said approximately determining said most apical point of the cochlea lacking acoustic hearing capability comprises:
  approximately determining said most apical point of the cochlea lacking acoustic hearing capability during introduction of said electrode array into the cochlea.

10. The method of claim 1, further comprising:
 applying an acoustic stimulation to the cochlea;
 recording a first electrically evoked compound potential (ECAP) in said one or more portions following said acoustic stimulation;
 applying an acoustic stimulation simultaneously with an electrical masking stimulation to the cochlea;
 recording a second ECAP in said one or more portions following said simultaneous stimulation; and
 comparing said first ECAP and said second ECAP.

11. The method of claim 10, wherein the method further comprises:
 selecting, based on said objective assessment, which of said plurality of electrodes are to be used to apply said electrical stimulation to the cochlea.

12. A method of determining a patient map utilized to control application of electrical stimulation to a cochlea having residual acoustic hearing capability, the method comprising:
 measuring a neural response of one or more portions of the cochlea to delivered stimulation;
 objectively determining, based on said measured neural response, that at least one of said one or more portions of the cochlea have the capability to respond to non-electrical stimulation;
 defining said patient map so as to prevent application of electrical stimulation to said at least one portion of the cochlea.

13. The method of claim 12, wherein said patient map defines at least one minimum hearing threshold and at least one maximum comfort threshold, each threshold defined with reference to said measured neural response.

14. The method of claim 12, wherein said patient map further controls application of non-electrical stimulation to the cochlea.

15. The method of claim 13, wherein said patient map further defines a timing of application of electrical stimulation to the cochlea so as to provide for application of said electrical stimulation to the cochlea substantially simultaneously with application of non-electrical stimulation to the cochlea.

16. A method for fitting a hearing prosthesis to the cochlea of a recipient having residual hearing, the method comprising:
 introducing one or more electrodes into the cochlea;
 applying a stimulation signal to the cochlea via at least one of the one or more electrodes;
 objectively assessing the residual hearing capability of one or more portions of the cochlea based on a measured neural response of said one or more portions to said stimulation signal;
 positioning at least one of the one or more electrodes in said cochlea so as to stimulate at least one of said one or more portions of the cochlea lacking residual hearing capability;
 at least partially implanting an electrode array having a plurality of electrodes therein in the cochlea;
 applying an electrical stimulation to the cochlea;
 recording a first electrically evoked compound potential (ECAP) in said one or more portions of the cochlea following said electrical stimulation;
 applying an electrical stimulation simultaneously with an acoustic masking stimulation to the cochlea;
 recording a second ECAP in said one or more portions following said simultaneous stimulation; and
 comparing said first ECAP and said second ECAP.

17. The method of claim 16, further comprising:
 fully implanting said electrode array in the recipient so as to position said at least one of said plurality of electrodes to deliver electrical stimulation to said one or more portions of the cochlea; and
 objectively assessing the acoustic hearing capability of said one or more portions of the cochlea following implantation of said electrode array.

18. The method of claim 16, wherein applying a stimulation signal to the cochlea comprises applying an acoustic stimulation signal to the cochlea; and
 wherein the method further comprises:
  measuring a neural response of said one or more portions of the cochlea to said acoustic stimulation signal.

19. The method of claim 16, wherein applying a stimulation signal to the cochlea comprises applying an electrical stimulation signal to the cochlea; and
 wherein the method further comprises:
  measuring a neural response of said one or more portions of the cochlea to said electrical stimulation signal.

20. The method of claim 16, further comprising:
 approximately simultaneously delivering electrical stimulation signals and acoustic stimulation signals to the cochlea; and
 measuring a neural response of said one or more portions of the cochlea to said approximately simultaneous stimulation.

21. The method of claim 16, wherein following said assessment of said one or more portions, the method further comprises:
 withdrawing said electrode array from said recipient; and
 implanting a second electrode array having a plurality of electrodes therein into the cochlea such that at least one of said plurality of electrodes is positioned to deliver electrical stimulation to said one or more portions of the cochlea.

22. A method of fitting a bimodal hearing prosthesis to a recipient, comprising:
  applying a stimulation signal to the cochlea;
  objectively assessing the capability of one or more portions of the cochlea to respond to non-electrical stimulation based on a measured neural response of said one or more portions to said stimulation signal; and
  positioning one or more electrodes in the cochlea for stimulating at least one of said one or more portions at least partially lacking the capability to respond to non-electrical stimulation.

23. The method of claim 22, wherein a plurality of electrodes are positioned in the cochlea, and wherein the method further comprises
  determining which of said plurality of electrodes are to be used for stimulating the cochlea based on said objective assessment.

24. The method of claim 22, wherein the method further comprises:
  at least partially implanting an electrode array having one or more electrodes therein in the recipient.

25. The method of claim 24, further comprising applying a non-electrical stimulation signal to the cochlea in the form of an acoustic stimulation signal; and wherein the method further comprises:
  measuring a neural response of said one or more portions of the cochlea to said acoustic stimulation signal.

26. The method of claim 24, further comprising:
  approximately simultaneously delivering an electrical stimulation and a non-electrical stimulation signal in the form of an acoustic stimulation to the cochlea; and
  measuring a neural response of said one or more portions to said approximately simultaneous stimulation.

27. The method of claim 24, further comprising:
  applying an electrical stimulation to the cochlea;
  recording a first electrically evoked compound potential (ECAP) in said one or more portions following said electrical stimulation;
  applying an electrical stimulation simultaneously with an acoustic masking stimulation to the cochlea;
  recording a second ECAP in said one or more portions following said simultaneous stimulation; and
  comparing said first ECAP and said second ECAP.

28. The method of claim 24, further comprising:
  applying an acoustic stimulation to the cochlea;
  recording a first electrically evoked compound potential (ECAP) in said one or more portions following said acoustic stimulation;
  applying an acoustic stimulation simultaneously with an electrical masking stimulation to the cochlea;
  recording a second ECAP in said one or more portions following said simultaneous stimulation; and
  comparing said first ECAP and said second ECAP.

29. The method of claim 24, wherein positioning said one or more electrodes so as to apply electrical stimulation to portions of the cochlea at least partially lacking the capability to respond to non-electrical stimulation comprises:
  explanting said electrode array; and
  implanting a second electrode array having one or more electrodes therein into said cochlea so that said one or more electrodes of said second electrode array are positioned to apply said electrical stimulation.

30. A method for fitting a hearing prosthesis configured to apply acoustic and electrical stimulation to the cochlea of a recipient having residual hearing, the method comprising:
  at least partially implanting an electrode array in the cochlea;
  applying a first stimulation to the cochlea;
  recording a first electrically evoked compound potential (ECAP) in at least one portion of the cochlea following said first stimulation;
  applying the first stimulation simultaneously with a masking stimulation to the cochlea;
  recording a second ECAP in said at least one portion following said simultaneous stimulation; and
  comparing said first ECAP and said second ECAP to determine whether said at least one portion of the cochlea has residual hearing capability; and
  positioning one or more electrodes in the cochlea for stimulating one or more portions of the cochlea lacking residual hearing capability.

31. The method of claim 30, wherein the first stimulation is electrical stimulation applied by the electrode array and the masking stimulation is an acoustic masking stimulation.

32. The method of claim 30, wherein the first stimulation is acoustic stimulation and the masking stimulation is an electrical masking stimulation applied by the electrode array.

33. The method of claim 30, wherein the method further comprises:
  based on said determination whether said at least one portion of the cochlea has residual hearing capability, selecting which of the one or more electrodes are to be used for stimulating to the cochlea.

34. The method of claim 30, wherein, the method further comprises:
  following said determination whether said at least one portion of the cochlea has residual hearing capability, withdrawing said electrode array from said recipient; and
  implanting a second electrode array in the cochlea configured to provide said electrical stimulation to said portions lacking residual hearing capability.

35. The method of claim 30, wherein comparing said first ECAP and said second ECAP to determine whether said at least one portion of the cochlea has residual hearing capability further comprises:
  fully implanting said electrode array in the recipient to stimulate to the cochlea; and
  objectively determining said portions of the cochlea having residual hearing capability following implantation of said electrode array.

36. A method of fitting a cochlear prosthesis to a cochlea having residual acoustic hearing capability, comprising:
  at least partially implanting an electrode array having one or more electrodes therein into the cochlea;
  applying stimulation to the cochlea via at least one of the one or more electrodes;
  applying non-electrical stimulation to the cochlea;
  objectively assessing the acoustic hearing capability of one or more portions of the cochlea based on a measured neural response of said one or more portions to said stimulations; and
  positioning the electrode array in the cochlea such that at least one of said one or more electrodes is adjacent a portion of the cochlea lacking the capability to respond to non-electrical stimulation based on the measured neural response.

* * * * *